US006518457B1

(12) United States Patent
Sakata et al.

(10) Patent No.: US 6,518,457 B1
(45) Date of Patent: Feb. 11, 2003

(54) UREA SYNTHESIS PROCESS

(75) Inventors: Eiji Sakata, Chiba (JP); Yasuhiko Kojima, Chiba (JP)

(73) Assignee: Tokyo Engineering Corporation, Tokyo (JP)

( * ) Notice: Subject to any disclaimer, the term of this patent is extended or adjusted under 35 U.S.C. 154(b) by 0 days.

(21) Appl. No.: 10/198,962

(22) Filed: Jul. 22, 2002

(30) Foreign Application Priority Data

Jul. 23, 2001 (JP) ........................................ 2001-221656

(51) Int. Cl.⁷ ............................................. C07C 273/04
(52) U.S. Cl. ............................ 564/67; 564/70; 564/71; 564/72
(58) Field of Search .............................. 564/67, 70, 71, 564/72

(56) References Cited

U.S. PATENT DOCUMENTS 6,114,579 A * 9/2000 Van Wijck .................. 564/67

FOREIGN PATENT DOCUMENTS

| JP | 61-109760 | 5/1986 |
| JP | 62-15070 | 4/1987 |
| JP | 10-182587 | 7/1998 |

\* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A process for the synthesis of urea, which comprises subjecting a urea synthesis solution from a urea synthesis column to stripping with a raw material carbon dioxide under a pressure approximately equal to the urea synthesis pressure to separate a major portion of unreacted ammonia and carbon dioxide as a mixed gas from the urea synthesis solution, condensing the mixed gas by indirect heat exchange with the urea synthesis solution from which the mixed gas was separated and that is preferably decompressed to a pressure lower than the urea synthesis pressure, and heating the urea synthesis solution by heat of condensation generated at the time of the condensation of the mixed gas.

7 Claims, 4 Drawing Sheets

UREA SYNTHESIS PROCESS

BACKGROUND OF THE INVENTION

1. Field of the Invention

The present invention relates to an improved urea synthesis process, and more particularly to a urea synthesis process wherein heat is recovered and utilized for decomposing unreacted ammonium carbamate contained in a urea solution.

2. Description of the Related Art

With regard to a method for recovering heat in a urea synthesis process, the present applicant has already proposed some methods in e.g. Japanese Patent Examined Publication No. 62-15070, Japanese Patent Laid-Open Nos. 61-109760 and 10-182587.

Figure 3:
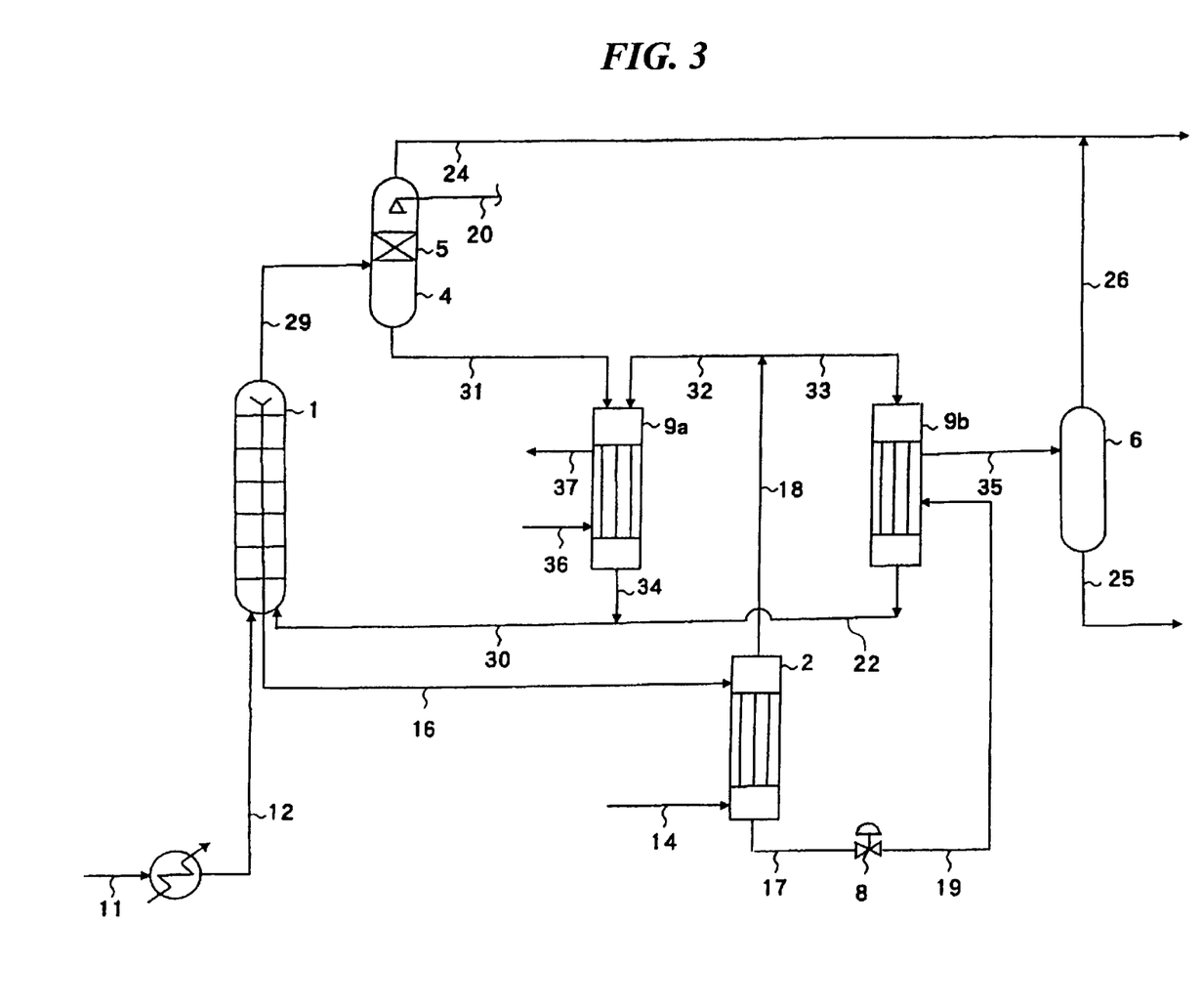
FIG. 3 is a process flow sheet showing a prior art technique.

In the method disclosed in the above listed Japanese Patent Examined Publication No. 62-15070 or Japanese Patent Laid-Open No. 61-109760, as shown in FIG. 3, a mixed gas separated from a urea synthesis solution in a stripper 2 is divided and supplied separately to the tube side of each of two shell-and-tube type vertical condensers 9a and 9b which are located in parallel, throughlines 18, and 32 and 33 so that the mixed gas is condensed. In the vertical condenser 9a, water is supplied to a shell side thereof through a line 36 and low pressure steam is generated through a line 37 by heat generated by condensation of the mixed gas. In the vertical condenser 9b, aurea solution comprising unseparated unreacted ammonia and unreacted carbon dioxide fed from the stripper 2 is heated at a shell side thereof by heat generated by condensation of the mixed gas, so that the heat is used as a heat source in a step of separating unreacted ammonia and unreacted carbon dioxide in a urea synthesis process.

According to this method, the condensation temperature of the mixed gas comprising ammonia, carbon dioxide and water, which is brought from the stripper 2, is 170° C. to 180° C. Since this temperature is higher than the temperature of the low pressure steam, which is 150° C. to 155° C., the temperature of a heated side can be kept higher and thereby heat recovery can efficiently be carried out. In addition, it is also possible to install a medium pressure decomposer, reboiler or falling film heater (not shown) in stead of the vertical condenser 9b to recover heat in the same manner.

However, in the case of the above described heat recovery, because of the increased number of devices used for urea production, the necessity of distribution of a mixed gas to two vertical condensers, etc., a urea synthesis system becomes complicated. Moreover, when condensation of the mixed gas is carried out on the tube side of the vertical condenser, due to thin-film condensation occurred on the tube surface, the heat transfer performance becomes lower and the heat transfer area becomes larger when compared with the bubble column type vertical condensation reactor described in Japanese Patent Laid-Open No. 10-182587. This results in upsizing of a vertical condenser, a high production cost of devices, and by extension, expensive construction cost. Furthermore, by this method, the mixed gas is supplied to the tube side of each of the vertical condensers 9a and 9b whereas a cooling medium is supplied to the shell side, and therefore this method is not structurally suitable for dividing the shell side, supplying a plurality of cooling mediums and performing heat exchange with each of them.

Figure 4:
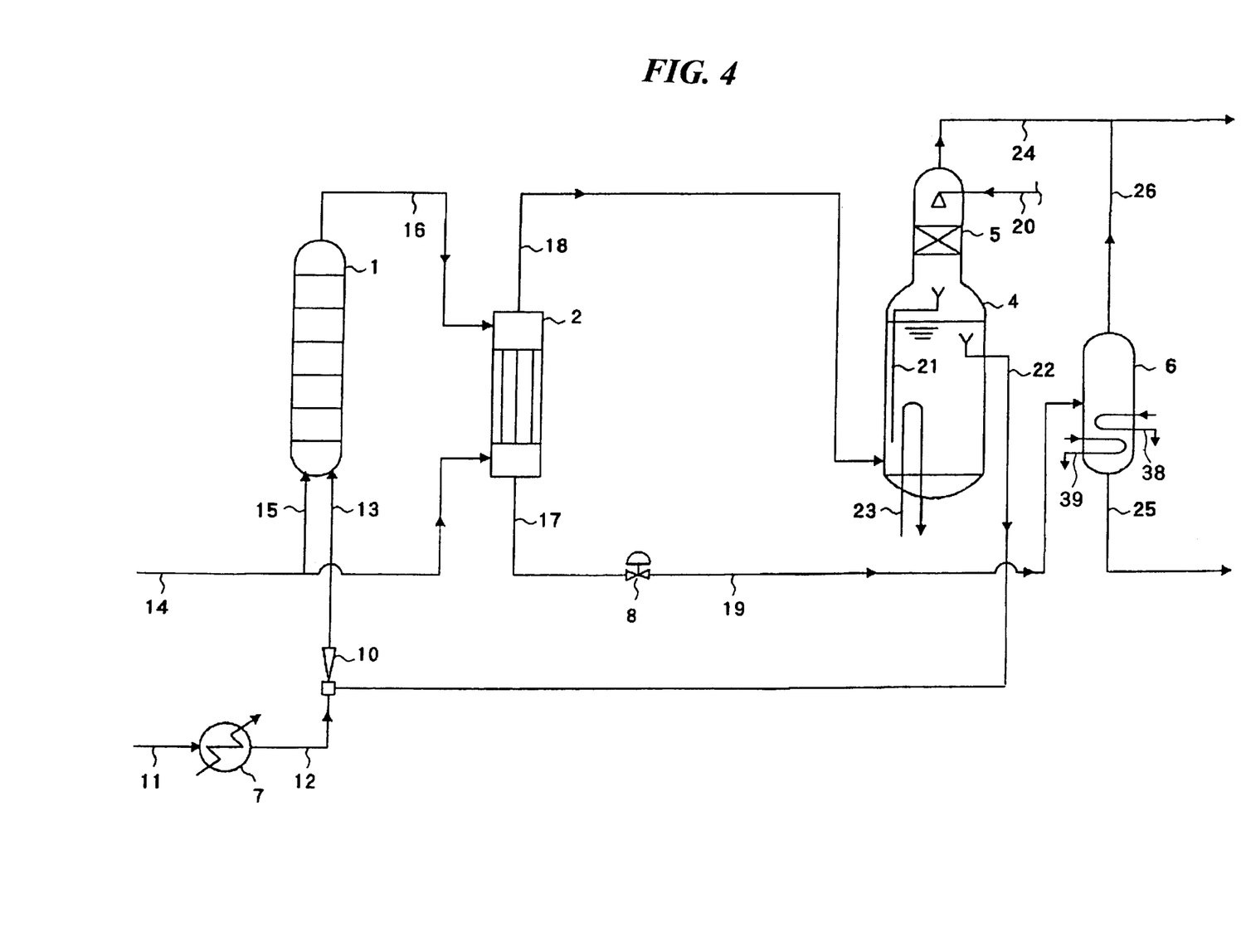
FIG. 4 is a process flow sheet showing another prior art technique.

In the above Japanese Patent Laid-Open No. 10-182587, as shown in FIG. 4, the mixed gas discharged from the stripper 2 to the line 18 is supplied to a vertical condensation reactor 4 having a cooling tube 23 therein and is then condensed, and the obtained heat of condensation is recovered by generating a low pressure steam in the cooling tube 23. The generated low pressure steam is used in a step of separating unreacted ammonia and carbon dioxide under a low pressure or in a step of concentrating a urea solution in a urea synthesis process.

However, when the recovered low pressure steam having a low temperature is used, it becomes difficult to maintain a temperature difference for heating in a step of separating unreacted ammonia and carbon dioxide, which requires a high temperature, and therefore it is required to enlarge the heat transfer area of a heater of a separator.

As described above, the prior art regarding a heat recovery method in a urea synthesis process has various problems to be solved.

SUMMARY OF THE INVENTION

It is an object of the present invention to provide a method for effectively recovering heat in a urea synthesis process so as to sharply reduce a heat transfer area, which is required in a urea production process as a whole.

As a result of concentrated studies to solve the above mentioned problems of the prior art, the present inventors have found that, when the heat of condensation of a mixed gas of ammonia and carbon dioxide having a high temperature, that is, a high temperature of 170° C. to 180° C., is directly used as a heat source in a step of separating unreacted ammonia and carbon dioxide, without generating a low pressure steam, in other words, without reducing the temperature to 150° C. to 155° C. that is the temperature of the low pressure steam, heat transfer efficiency is substantially improved and the heat transfer area required in a urea synthesis process as a whole is sharply reduced, thereby completing the present invention.

The present invention provides the following urea synthesis process:

A urea synthesis process, which comprises the steps of, reacting raw material ammonia and carbon dioxide in a urea synthesis column at a urea synthesis temperature and under a urea synthesis pressure; contacting the resulting urea synthesis solution comprising urea, unreacted ammonia, unreacted carbon dioxide and water with at least a portion of the raw material carbon dioxide under heating in a stripper under a pressure approximately equal to the urea synthesis pressure, thereby separating unreacted ammonia and unreacted carbon dioxide as a mixed gas of ammonia, carbon dioxide and water; feeding the mixed gas to a shell side of a vertical condensation reactor having a cooling tube therein to contact the mixed gas with an absorption medium under cooling for condensation of the mixed gas; and recycling the resulting condensate to the urea synthesis column so as to obtain a urea synthesis solution comprising unreacted ammonia and unreacted carbon dioxide that have not been separated, wherein the urea synthesis solution separated from the mixed gas in the stripper is fed to the cooling tube of the vertical condensation reactor, while supplying the mixed gas separated from the urea synthesis solution in the stripper is fed to the shell side of the vertical condensation reactor so as to condense the mixed gas by indirect heat exchange with the urea synthesis solution in the cooling tube; and the urea synthesis solution is heated in the cooling tube by the heat of condensation generated at the time of the condensation of the mixed gas.

It is preferable that the urea synthesis solution comprising unseparated unreacted ammonia and unreacted carbon dioxide discharged from the stripper is decompressed to a pressure lower than the urea synthesis pressure, and is then fed to the cooling tube of the vertical condensation reactor.

It is preferable that the urea synthesis solution comprising unseparated unreacted ammonia and unreacted carbon dioxide discharged from the stripper is decompressed and fed to a medium pressure separator wherein a portion of unreacted ammonia and unreacted carbon dioxide contained in the urea synthesis solution is separated, and then the resulting solution is fed to the cooling tube of the vertical condensation reactor.

The urea synthesis solution fed to the cooling tube side of the vertical condensation reactor is preferably heated to a temperature of 150° C. to 170° C. by the heat of condensation of the mixed gas fed to the vertical condensation reactor.

The cooling tube of the vertical condensation reactor is preferably a U-shaped tube having multi channels.

DETAILED DESCRIPTION OF THE PREFERRED EMBODIMENTS

In the present invention, a urea synthesis solution (hereinafter, simply referred to as aurea solution) containing remaining unreacted ammonia and unreacted carbon dioxide discharged from a bottom part of a stripper is preferably fed to the cooling tube of a vertical condenser after being decompressed through a reducing valve. This is because a temperature difference between the urea solution fed to the cooling tube of the vertical condenser and a condensate contained in the shell side thereof can be kept large by a decrease in temperature of the urea solution by decompression. At this time, the pressure is reduced to a medium pressure within a range of preferably about 0.01 to 3.0 MPa, more preferably about 1.0 to 2.5 MPa, and particularly preferably about 1.5 to 2.0 MPa. It is preferable that the urea solution, the pressure of which is reduced to a medium pressure, leaves a mixed gas comprising ammonia, carbon dioxide and water separated from the solution by decompression, in a medium pressure separator, before entering the cooling tube. By removing the separated mixed gas and feeding only the urea solution to the cooling tubes, the urea solution can equally be distributed to each tube and heat exchange efficiency is improved.

A vertical condensation reactor is preferably a vertical heat exchanger comprising a U-shaped cooling tube having multi channels. By using this vertical condensation reactor, not only the heating of the urea solution from the stripper, but also the generation of a low pressure steam and the heating of other cooling mediums such as a raw material liquid ammonia, can easily be carried out without increasing the number of devices and/or distributing the gas.

The present invention will be explained in detail with reference to drawings.

Figure 1:
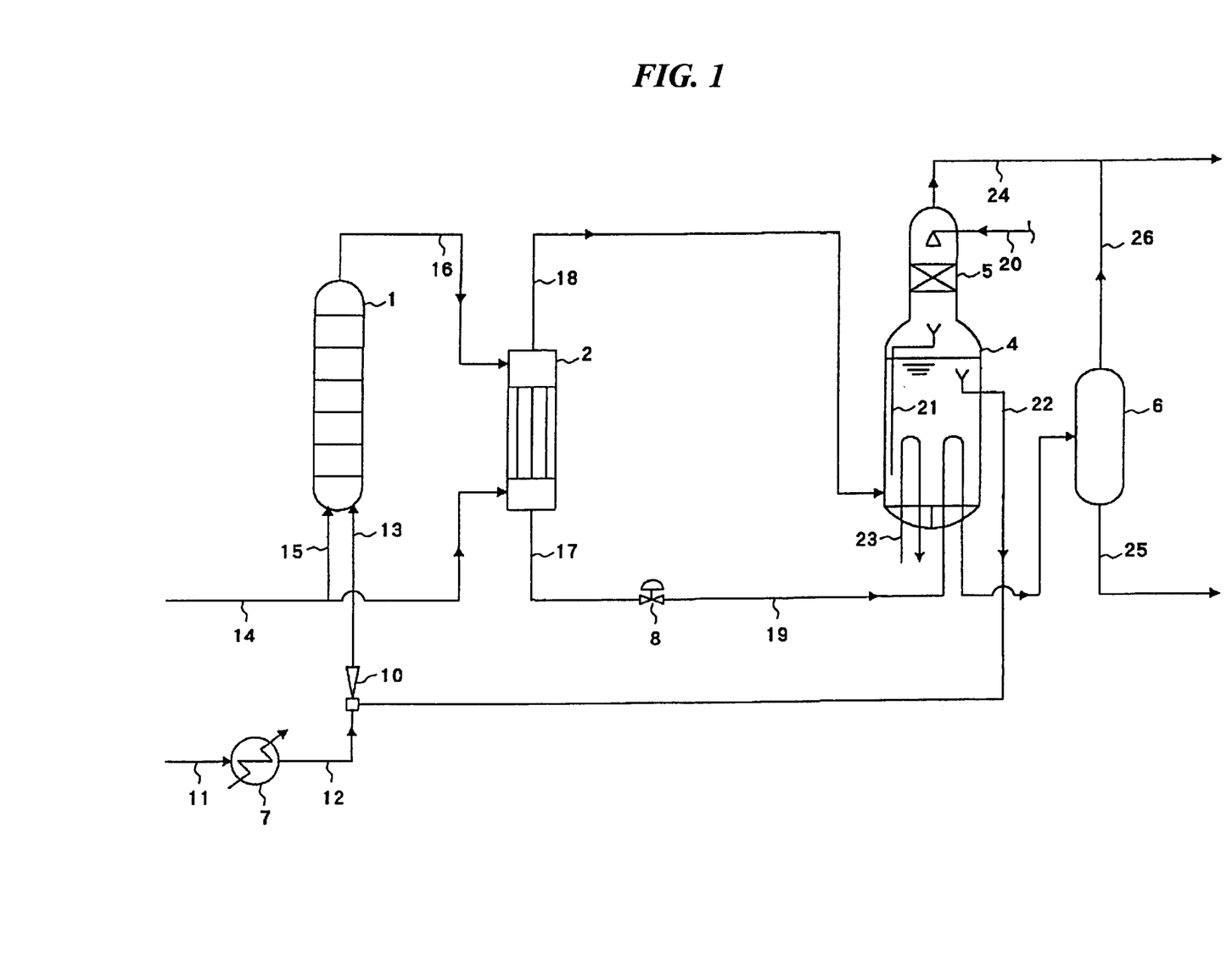
FIG. 1 is a process flow sheet showing one embodiment of the present invention.

FIG. 1 is a process flow sheet showing one embodiment of the present invention.

A raw material ammonia, after the pressure is raised to about 25 MPa, is fed to a heat exchanger 7 through a line 11, and heated to about 175° C. with a recovered low pressure steam and a condensate of a high pressure steam. Subsequently, the ammonia is fed to an ejector 10 through a line 12 and then expanded to the urea synthesis pressure. A condensate fed from a down pipe 22 is sucked to the ejector, and then it is fed to a urea synthesis column 1 together with the ammonia through a line 13.

The raw material carbon dioxide and anti-corrosive air are supplied to a bottom part of the stripper 2 through a line 14, but a portion of them is fed to the urea synthesis column 1 though the line 15.

While ammonia, carbon dioxide and anti-corrosive air are going up in the urea synthesis column 1, which is operated under a pressure of 13 to 25 MPa at a temperature of 180° C. to 200° C., aurea synthesis reaction proceeds. After completion of the reaction, the urea synthesis solution is discharged from a top part of the urea synthesis column 1 to a line 16, and is then fed to a top part of the stripper 2.

In the stripper 2 operated under a pressure of 13 to 25 MPa at a temperature of 160° C. to 200° C., unreacted ammonium carbamate (unreacted ammonia and unreacted carbon dioxide) contained in the urea synthesis solution are thermally decomposed and separated as a mixed gas comprising ammonia, carbon dioxide, water and inert gas.

The above mixed gas is fed from the top part of the stripper 2 to a shell side of the vertical condensation reactor 4 through the line 18, while the urea synthesis solution comprising unseparated unreacted ammonia and unreacted carbon dioxide is discharged from the bottom part of the stripper 2 to a line 17 and then fed to a cooling tube side of the vertical condensation reactor 4 after decompressed through a reducing valve 8 to a pressure of 1.0 to 2.5 MPa.

In the vertical condensation reactor 4, the pressure of a recovery solution (a solution obtained by separating the unreacted ammonium carbamate contained in the urea synthesis solution fed from the stripper 2 as a mixed gas comprising ammonia, carbon dioxide and water under a medium and/or low pressure and absorbing the mixed gas into water, diluted ammonia water or the like), which is fed as an absorption medium through a line 20, is raised to about 13.5 to 25.5 MPa at a temperature of about 110° C., and then fed to a packed part 5 installed on a top part of the vertical condensation reactor 4. The packed part 5 is operated under a pressure of 13 to 25 MPa at a temperature of 160° C. to 190° C. An absorption solution discharged from a bottom part of the packed part 5 flows down from a down pipe 21 to a bottom part of the vertical condensation reactor 4, and then contacted with the mixed gas brought from the line 18 under cooling so as to absorb and condense the mixed gas. The shell side of the vertical condensation reactor 4 is filled with the above absorption solution and condensate (hereinafter, both solutions are collectively referred to as a condensate) fed from the packed part 5, and heat of condensation (absorption heat) is removed by a cooling medium, which is fed to a cooling tube 19 and, if desired, to a cooling tube 23.

As described above, the vertical condensation reactor 4 is a vertical heat exchanger comprising a U-shaped cooling tube having multi channels, which not only heats a urea solution supplied from a stripper but also preferably supplies water to other channels to generate low pressure steam. Moreover, this vertical condensation reactor 4 can easily heat other cooling mediums such as a raw material liquid ammonia.

The temperature of the shell side of the vertical condensation reactor 4 is controlled at 170° C. to 190° C., and this control of temperature can be carried out by removing the heat of condensation of a mixed gas preferably by heating two cooling mediums, for example, by heating the urea synthesis solution and generating steam.

The condensate in the shell side of the vertical condensation reactor 4 is fed to a sucking side of the ejector 10 through the down pipe 22 having an opening on the top part of the shell side.

The urea synthesis solution supplied to the cooling tube side of the vertical condensation reactor 4 through a line 19 is heated to a temperature of 150° C. to 170° C., which is desirable to decompose unreacted ammonium carbamate under a medium pressure. The heat required for medium pressure decomposition is provided from the heat of condensation generated in the vertical condensation reactor 4, and accordingly there is no need for the heating of a medium pressure decomposer 6.

The heated urea synthesis solution is fed to the medium pressure decomposer 6 operated preferably under a pressure of 1.0 to 2.5, more preferably under a pressure of 1.5 to 2.0 MPa at a temperature of 150° C. to 170° C. to separate unseparated unreacted ammonium carbamate. The urea solution comprising almost no unreacted ammonium carbamate is fed through a line 25 to a low pressure decomposer (not shown) for the next step. On the other hand, the mixed gas separated from the urea synthesis solution is subjected to a recovering step through a line 26.

The condensate generated by absorbing the mixed gas supplied from the line 18 flows down through the down pipe 22 by gravitation, and after the pressure is raised by an ejector 10, the condensate is fed to the urea synthesis column 1. On the other hand, the mixed gas which is not absorbed is subjected to the next step through a line 24.

Figure 2:
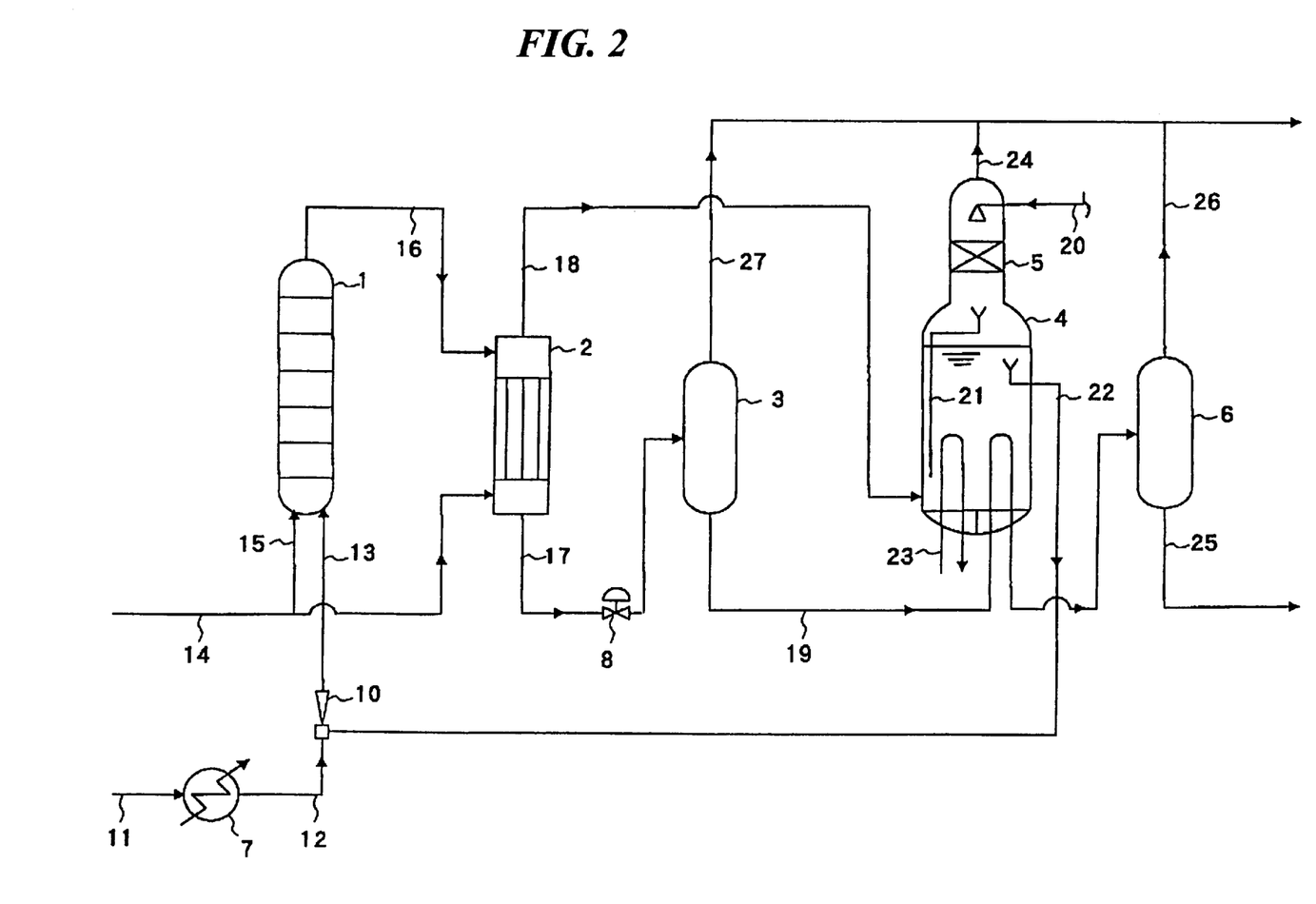
FIG. 2 is a process flow sheet showing another embodiment of the present invention.

FIG. 2 is a process flow sheet showing another embodiment of the present invention. A urea solution separated from a mixed gas in the stripper 2 is supplied to the medium pressure separator 3, and after the mixed gas contained in the urea solution is further separated, the resulting solution is fed to the cooling tube of the vertical condensation reactor 4.

The stripper 2 is operated under a pressure of 13 to 25 MPa at a temperature of 160° C. to 200° C., and therein, unreacted ammonium carbamate contained in the urea synthesis solution is decomposed into ammonia and carbon dioxide by stripping with a raw material carbon dioxide, and then separated as a mixed gas comprising ammonia, carbon dioxide, water and inert gas. This mixed gas is fed from the top part of the stripper 2 to the shell side of the vertical condensation reactor 4 through the line 18, while the urea solution comprising unseparated unreacted ammonia and unreacted carbon dioxide is discharged from the bottom part of the stripper 2 to the line 17, decompressed through reducing valve 8, and then fed to the medium pressure separator 3.

The medium pressure separator 3 is operated under a pressure of 1.5 to 2.5 MPa at a temperature of 120° C. to 150° C. Accordingly, the urea synthesis solution falls from the operation pressure and temperature of the stripper 2 to the operation pressure and temperature of the medium pressure separator 3 by adiabatic expansion and becomes two phases of gas and liquid, and thereby the gas contained in the urea solution is separated. The urea solution obtained by separation of gas from the urea synthesis solution is fed from the bottom part of the vertical condensation reactor 4 to the cooling tube side through the line 19, while the mixed gas separated from the urea solution is fed to a recovering step through a line 27.

In the vertical condensation reactor 4, the pressure of a recovery solution, which is supplied as an absorption medium from the line 20, is raised to about 13.5 to 25.5 MPa at a temperature of about 110° C., and then fed to the packed part 5 installed on the top part of the vertical condensation reactor 4. The packed part 5 is operated under a pressure of 13 to 25 MPa at a temperature of 160° C. to 190° C., and the solution accumulated in the bottom part of the filling part 5 is fed to the bottom part of the vertical condensation reactor 4 through the down pipe 21.

The shell side of the vertical condensation reactor 4 is filled with the absorption solution and condensate delivered from the filling part 5, and the mixed gas is absorbed and condensed and the heat of condensation is removed by the cooling tubes 19 and 23.

Since, in the medium pressure separator, the urea solution has a pressure lower than the pressure in the synthesis column and is separated into the two phases of gas and liquid, if it is directly fed to the cooling tubes, the distribution of the urea solution in each tube tends to be uneven. However, if the urea solution is fed to the vertical condensation reactor 4 after the mixed gas contained in the urea solution is separated in the medium pressure separator 3, the solution is evenly distributed to cooling tubes, and heat exchange efficiency is improved.

Regarding the urea synthesis solution fed to the tube side, considering improvement in heat transfer performance by even distribution of the solution to cooling tubes, it is preferable that the gas contained in the urea synthesis solution is separated in the medium pressure separator 3 and only the liquid phase is fed to the cooling tube side.

In the present invention, the embodiments shown in FIG. 1 and FIG. 2 can selectively be used as appropriate depending on the cost of the cooling tubes and the medium pressure separator 3. However, where a large-size vertical condensation reactor 4 is used, the cost of the equipment can be reduced somewhat by installation of the medium pressure separator 3.

The present invention will be further specifically described in the following Examples and Comparative Examples.

EXAMPLE 1

According to the process shown in FIG. 1, 1,725 tons/day of urea was synthesized.

The heat transfer area required for heating aurea solution from a stripper to 155° C. was found to be 285 m$^2$. This was about $\frac{2}{10}$ to $\frac{3}{10}$ of the heat transfer area required in the prior art. The material balance is shown in Table 1. In the table, the vertical column represents the number of each line shown in FIG. 1, and the horizontal column represents the pressure, the temperature, the flow rate and the composition of a substance flowing through each line. The shell side temperature, the tube side temperature, the total heat transfer coefficient and the required heat transfer area of a vertical condensation reactor are shown in Table 3.

As shown in Table 3, since it was possible to make the temperature difference between the shell side temperature and the tube side exit temperature in the vertical condensation reactor large and the total heat transfer coefficient was remarkably improved, the heat transfer area was significantly reduced when compared with the prior art.

EXAMPLE 2

According to the process shown in FIG. 2, 1,725 tons/day of urea was synthesized.

The heat transfer area required for heating a urea solution from a stripper to 155° C. after decompression was found to be 252 m². This was about 2/10 to 3/10 of the heat transfer area required in the prior art.

The material balance is shown in Table 1. In the table, the vertical column represents the number of each line shown in FIG. 2, and the horizontal column represents the pressure, the temperature, the flow rate and the composition of a substance flowing through each line. The shell side temperature, the tube side temperature, the total heat transfer coefficient and the required heat transfer area of a vertical condensation reactor are shown in Table 3.

As shown in Table 3, differing from Example 1, since only the urea synthesis solution is fed to the tube side after the separation of a mixed gas and urea solution, it became unnecessary to raise the temperature of the mixed gas. In addition, since the urea synthesis solution was evenly distributed, the total heat transfer coefficient was further improved and the heat transfer area was further reduced.

COMPARATIVE EXAMPLE 1

According to the process flow shown in FIG. 3, 1,725 tons/day of urea was synthesized.

The material balance is shown in Table 2. In the table, the vertical column represents the number of each line shown in FIG. 3, and the horizontal column represents the pressure, the temperature, the flow rate and the composition of a substance flowing through each line. The shell side temperature, the tube side temperature, the total heat transfer coefficient and the required heat transfer area of a vertical condensation reactor are shown in Table 3.

As shown in Table 3, although there could remain the temperature difference between the tube side temperature and the shell side outlet temperature in the vertical condensation reactor, the heat transfer area required for heating a urea solution from a stripper to 155° C. after decompression was found to be 1,028 m², since the total heat transfer coefficient was low due to falling film type condensation.

COMPARATIVE EXAMPLE 2

According to the process shown in FIG. 4, 1,725 tons/day of urea was synthesized.

The material balance is shown in Table 2. In the table, the vertical column represents the number of each line shown in FIG. 4, and the horizontal column represents the pressure, the temperature, the flow rate and the composition of a substance flowing through each line. The shell side temperature, the tube side temperature, the total heat transfer coefficient and the required heat transfer area of a vertical condensation reactor are shown in Table 3.

As shown in Table 3, the total heat transfer coefficient was greater than that in Comparative Example 1. However, since the temperature difference between the tube side temperature and the shell side outlet temperature in the vertical condensation reactor could not sufficiently be retained by using the recovered low pressure steam, heat transfer area required for heating a urea solution from a stripper to 155° C. after decompression was found to be 842 m².

According to the present invention, since the temperature of the condensation of a mixed gas is high under a synthesis pressure, indirect heat exchange is performed directly between a urea solution fed from a stripper (preferably after decompression) and a condensate by using the heat of condensation, which has been used for the generation of a low pressure steam in the prior art, thereby making it possible to efficiently recover heat required for medium pressure decomposition.

Although the heat of condensation of a mixed gas under a urea synthesis pressure is used as the heat source for medium pressure decomposition in the prior art process, the process becomes complicated in that the number of devices increases and the division of the mixed gas is required. In the present invention, since a vertical condensation reactor which is a vertical heat exchanger having a U-shaped cooling tube is used, it becomes possible to simultaneously carry out both the generation of a low pressure steam and the heating of a urea synthesis solution by dividing the tube sheet, without increasing the number of devices or without dividing the gas. According to the configuration of the heat exchanger, for example, other cooling mediums such as liquid ammonia and recovery solution can easily be introduced by dividing the tube sheet.

TABLE 1

1725MTPD Urea production

| | | Line number | Pressure MPa | Temperature ° C. | Flow rate T/D | Urea wt % | Ammonia wt % | Carbon dioxide wt % | Water wt % |
|---|---|---|---|---|---|---|---|---|---|
| Example 1 | | | | | | | | | |
| Raw material NH₃ | | 11 | 22.5 | 35 | 976 | 0.0 | 100.0 | 0.0 | 0.0 | 100.0 |
| Raw material CO₂ | | 14 | 15.5 | 135 | 1212 | 0.0 | 0.0 | 100.0 | 0.0 | 100.0 |
| Urea synthesis column outlet | | 16 | 15.5 | 185 | 5569 | 33.4 | 34.3 | 13.6 | 18.7 | 100.0 |
| Stripper outlet solution | | 17 | 15.5 | 172 | 3444 | 51.4 | 11.5 | 12.0 | 25.1 | 100.0 |
| After decompression | Solution | 19 | 1.75 | 139 | 3282 | 53.9 | 10.9 | 9.3 | 25.9 | 100.0 |
| | Gas | | 1.75 | 139 | 162 | 0 | 23.7 | 66.2 | 10.1 | 100.0 |
| After heating | Solution | 25 | 1.75 | 155 | 2870 | 61.8 | 7.2 | 3.6 | 27.4 | 100.0 |
| | Gas | 26 | 1.75 | 155 | 574 | 0 | 32.9 | 53.6 | 13.5 | 100.0 |
| Vertical condensation reactor outlet | | 22 | 15.5 | 180 | 4448 | 27.1 | 30.0 | 23.9 | 19.0 | 100.0 |
| Example 2 | | | | | | | | | |
| Raw material NH₃ | | 11 | 22.5 | 35 | 976 | 0.0 | 100.0 | 0.0 | 0.0 | 100.0 |
| Raw material CO₂ | | 14 | 15.5 | 135 | 1212 | 0.0 | 0.0 | 100.0 | 0.0 | 100.0 |

TABLE 1-continued

1725MTPD Urea production

|  |  | Line number | Pressure MPa | Temperature °C. | Flow rate T/D | Urea wt % | Ammonia wt % | Carbon dioxide wt % | Water wt % |  |
|---|---|---|---|---|---|---|---|---|---|---|
| Urea synthesis column outlet |  | 16 | 15.5 | 185 | 5559 | 33.4 | 34.3 | 13.6 | 18.7 | 100.0 |
| Stripper outlet solution |  | 17 | 15.5 | 172 | 3444 | 51.4 | 11.5 | 12.0 | 25.1 | 100.0 |
| After decompression and separation | Solution | 19 | 1.75 | 139 | 3282 | 53.9 | 10.9 | 9.3 | 25.9 | 100.0 |
|  | Gas | 27 | 1.75 | 139 | 162 | 0 | 23.7 | 66.2 | 10.1 | 100.0 |
| After heating | Solution | 25 | 1.75 | 155 | 2885 | 61.41 | 7.5 | 3.6 | 27.5 | 100.0 |
|  | Gas | 26 | 1.75 | 155 | 398 | 0 | 35.7 | 50.5 | 13.8 | 100.0 |
| Vertical condensation reactor outlet |  | 22 | 15.5 | 180 | 4448 | 27.1 | 30.0 | 23.9 | 19.0 | 100.0 |

TABLE 2

1725MTPD Urea production

|  |  | Line number | Pressure MPa | Temperature °C. | Flow rate T/D | Urea wt % | Ammonia wt % | Carbon dioxide wt % | Water wt % |  |
|---|---|---|---|---|---|---|---|---|---|---|
| Comparative Example 1 |  |  |  |  |  |  |  |  |  |  |
| Raw material NH₃ |  | 11 | 18.0 | 35 | 976 | 0.0 | 100.0 | 0.0 | 0.0 | 100.0 |
| Raw material CO₂ |  | 14 | 18.0 | 135 | 1212 | 0.0 | 0.0 | 100.0 | 0.0 | 100.0 |
| Urea synthesis column outlet |  | 16 | 17.5 | 190 | 5746 | 32.3 | 36.7 | 11.8 | 19.2 | 100.0 |
| Stripper outlet solution |  | 17 | 17.5 | 178 | 3659 | 48.4 | 13.0 | 13.8 | 24.8 | 100.0 |
| After decompression | Solution | 19 | 1.75 | 136 | 3435 | 51.6 | 12.2 | 10.5 | 25.7 | 100.0 |
|  | Gas |  | 1.75 | 136 | 224 | 0 | 26.1 | 83.8 | 10.1 | 100.0 |
| After heating | Solution | 25 | 1.75 | 155 | 2890 | 61.3 | 7.4 | 3.6 | 27.7 | 100.0 |
|  | Gas | 26 | 1.75 | 155 | 769 | 0 | 34.3 | 52.0 | 13.7 | 100.0 |
| Vertical condenser outlet | Solution | 22 | 17.5 | 175 | 3520 | 0.1 | 39.7 | 44.4 | 15.8 | 100.0 |
|  | Gas | 30 | 17.5 | 175 | 1462 | 0 | 64 | 35.8 | 0.2 | 100.0 |
| Comparative Example 2 |  |  |  |  |  |  |  |  |  |  |
| Raw material NH₃ |  | 11 | 22.5 | 35 | 976 | 0.0 | 100.0 | 0.0 | 0.0 | 100.0 |
| Raw material CO₂ |  | 14 | 15.5 | 135 | 1212 | 0.0 | 0.0 | 100.0 | 0.0 | 100.0 |
| Urea synthesis column outlet |  | 16 | 15.5 | 105 | 5509 | 33.4 | 34.3 | 13.6 | 18.7 | 100.0 |
| Stripper outlet solution |  | 17 | 15.5 | 172 | 3444 | 51.4 | 11.5 | 12.0 | 25.1 | 100.0 |
| After decompression | Solution | 19 | 1.75 | 139 | 3282 | 53.9 | 10.9 | 9.3 | 25.9 | 100.0 |
|  | Gas |  | 1.75 | 139 | 162 | 0 | 23.7 | 66.2 | 10.1 | 100.0 |
| After heating | Solution | 25 | 1.75 | 155 | 2885 | 61.41 | 7.5 | 3.6 | 27.5 | 100.0 |
|  | Gas | 26 | 1.75 | 155 | 398 | 0 | 35.7 | 50.5 | 13.8 | 100.0 |
| Vertical condensation reactor outlet |  | 22 | 15.5 | 180 | 4448 | 27.1 | 30.0 | 23.9 | 19.0 | 100.0 |
| Heater steam |  | 38 | 0.6 | 155 | 333 | 0.0 | 0.0 | 0.0 | 100.0 | 100.0 |
| Heater condensate |  | 39 | 2.0 | 214 | 1108 | 0.0 | 0.0 | 0.0 | 100.0 | 100.0 |

TABLE 3

|  |  | Example 1 | Example 2 | Comparative Example 1 | Comparative Example 2 Recovered low pressure steam | Comparative Example 2 Medium pressure condensate | Total |
|---|---|---|---|---|---|---|---|
| Shell side Temperature (inlet) | °C. | 180 | 180 | 136 | 139 | 149 |  |
| Shell side Temperature (outlet) | °C. | 180 | 180 | 155 | 149 | 155 |  |

TABLE 3-continued

| | | Example 1 | Example 2 | Comparative Example 1 | Comparative Example 2 Recovered low pressure steam | Comparative Example 2 Medium pressure condensate | Total |
|---|---|---|---|---|---|---|---|
| Tube side temperature (inlet) | °C. | 139 | 139 | 180 | 155 | 214 | |
| Tube side temperature (outlet) | °C. | 155 | 155 | 175 | 155 | 158 | |
| Total heat transfer coefficient | Kcal/m$^2$/Hr/°C. | 1000 | 1100 | 380 | 950 | 800 | |
| Required heat transfer area | m$^2$ | 285 | 252 | 1028 | 672 | 170 | 842 |

What is claimed is:

1. In a urea synthesis process, which comprises the steps of reacting raw material ammonia and carbon dioxide in a urea synthesis column at a urea synthesis temperature and pressure; contacting the resulting urea synthesis solution comprising urea, unreacted ammonia, unreacted carbon dioxide and water with at least a portion of the raw material carbon dioxide under heating in a stripper under a pressure approximately equal to the urea synthesis pressure, thereby separating unreacted ammonia and unreacted carbon dioxide as a mixed gas of ammonia, carbon dioxide and water; feeding the mixed gas to a shell side of a vertical condensation reactor having a cooling tube therein to contact the mixed gas with an absorption medium under cooling thereby condensing the mixed gas; and recycling the resulting condensate to the urea synthesis column so as to obtain a urea synthesis solution comprising unreacted ammonia and unreacted carbon dioxide that have not been separated, the steps comprising feeding the urea synthesis solution separated from the mixed gas in said stripper to the cooling tube side of said vertical condensation reactor, while feeding the mixed gas separated from the urea synthesis solution in said stripper to the shell side of said vertical condensation reactor so as to condense the mixed gas by indirect heat exchange with the urea synthesis solution in said cooling tube side; and heating the urea synthesis solution in said cooling tube side by the heat of condensation generated at the time of the condensation of said mixed gas.

2. The process according to claim 1, wherein the urea synthesis solution comprising unseparated unreacted ammonia and unreacted carbon dioxide discharged from said stripper is decompressed to a pressure lower than the urea synthesis pressure, and is then fed to the cooling tube side of said vertical condensation reactor.

3. The process according to claim 2, wherein said urea synthesis solution is decompressed to a pressure of from 1.0 to 2.5 Mpa.

4. The process according to claim 1, wherein the urea synthesis solution comprising unseparated unreacted ammonia and unreacted carbon dioxide discharged from said stripper is decompressed and fed to a medium pressure separator to separate a portion of unreacted ammonia and unreacted carbon dioxide contained in the urea synthesis solution, the resulting solution is then fed to the cooling tube side of said vertical condensation reactor.

5. The process according to claim 4, wherein said urea synthesis solution is decompressed to a pressure of from 1.0 to 2.5 Mpa.

6. The process according to claim 1, wherein said urea synthesis solution fed to the cooling tube side of said vertical condensation reactor is heated to a temperature of 150° C. to 170° C. by the heat of condensation of said mixed gas fed to said vertical condensation reactor.

7. The process according to claim 1, wherein the cooling tube side of said vertical condensation reactor comprises a U-shaped tube having multi channels.

* * * * *

UNITED STATES PATENT AND TRADEMARK OFFICE
CERTIFICATE OF CORRECTION

PATENT NO.    : 6,518,457 B1
DATED         : February 11, 2003
INVENTOR(S)   : Sakata et al.

It is certified that error appears in the above-identified patent and that said Letters Patent is hereby corrected as shown below:

<u>Title page,</u>
Item [73], Assignee, should read:
-- [73] Assignee:    Toyo Engineering Corporation,
                     Tokyo (JP) --

Signed and Sealed this

Fifth Day of August, 2003

JAMES E. ROGAN
*Director of the United States Patent and Trademark Office*